(12) United States Patent
Alam

(10) Patent No.: US 6,217,772 B1
(45) Date of Patent: Apr. 17, 2001

(54) METHOD AND A DEVICE FOR DIALYSIS OF LIQUID SAMPLES

(76) Inventor: Aftab Alam, 500 Clayton Meadows, St. Louis, MO (US) 63011

( * ) Notice: Subject to any disclaimer, the term of this patent is extended or adjusted under 35 U.S.C. 154(b) by 0 days.

(21) Appl. No.: 09/192,999

(22) Filed: Nov. 16, 1998

Related U.S. Application Data

(63) Continuation-in-part of application No. 08/840,221, filed on Apr. 11, 1997, now abandoned.
(60) Provisional application No. 60/070,119, filed on Dec. 31, 1997.

(51) Int. Cl.[7] ............................. B01D 61/24; B01D 61/28; B01D 21/26
(52) U.S. Cl. ...................... 210/644; 210/232; 210/242.1; 210/257.2; 210/321.6; 210/787; 436/177; 436/178
(58) Field of Search .................................. 210/232, 242.1, 210/321.6, 257.2, 321.72, 644, 645, 787; 422/101, 102; 436/177, 178

(56) References Cited

U.S. PATENT DOCUMENTS 4,450,076 * 5/1984 Medicus et al. .................. 210/242.1

* cited by examiner

*Primary Examiner*—John Kim
(74) *Attorney, Agent, or Firm*—Arent Fox Kintner Plotkin & Kahn, PLLC

(57) ABSTRACT

A method and a device for dialysis having a dialysis reservoir and a collection reservoir. A sample is placed in the dialysis reservoir for dialysis. After dialysis, dialysis reservoir is centrifuged and the dialyzed sample is collected in the collection reservoir.

20 Claims, 5 Drawing Sheets

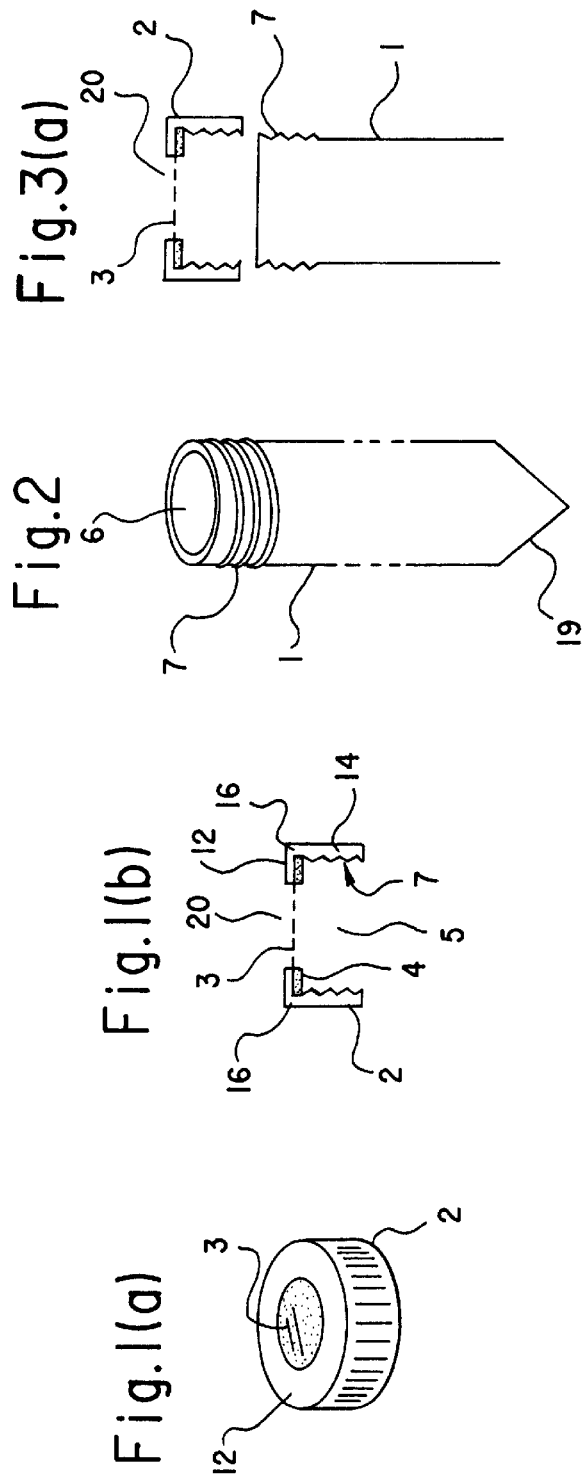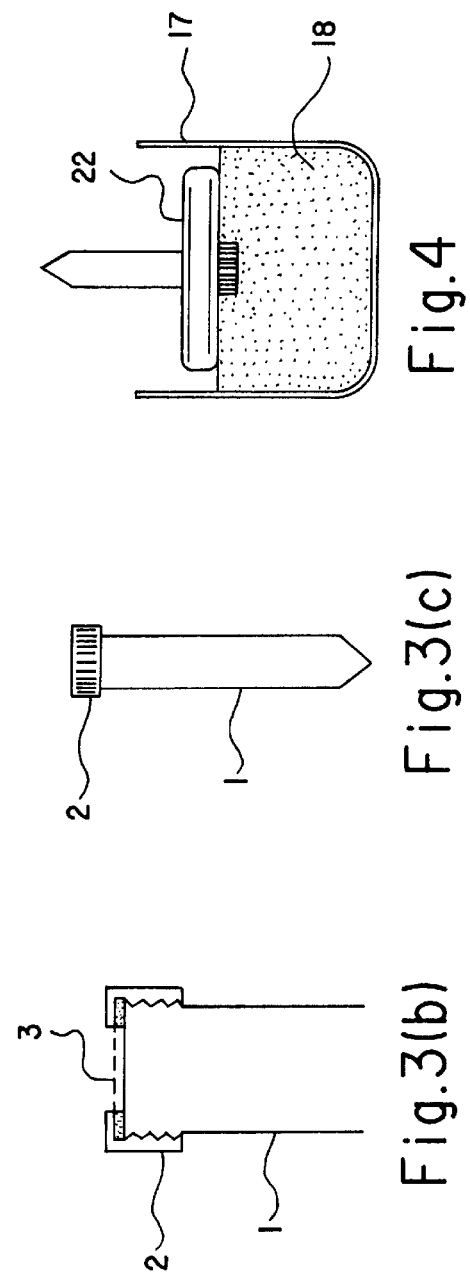

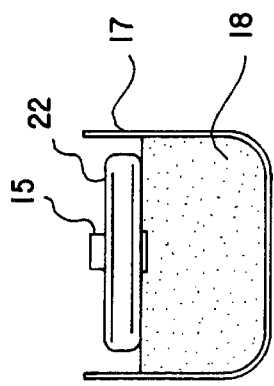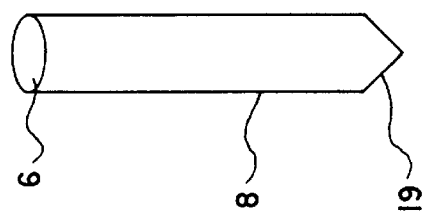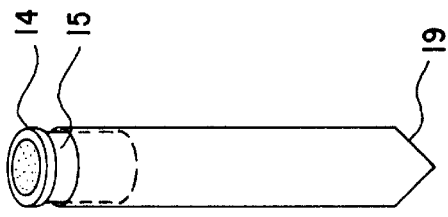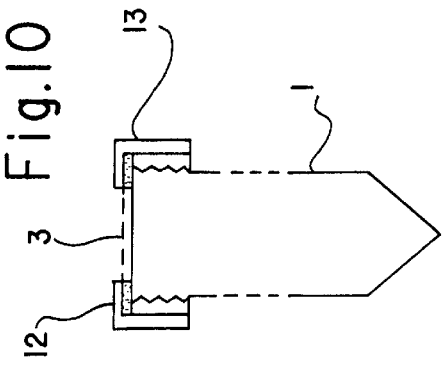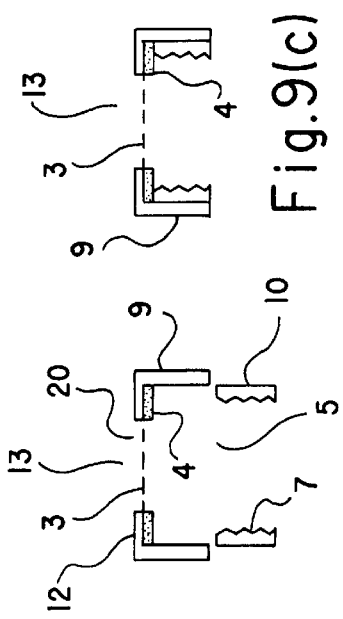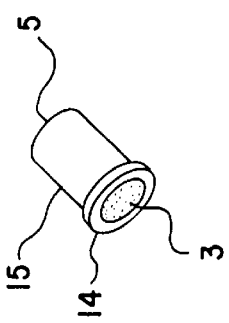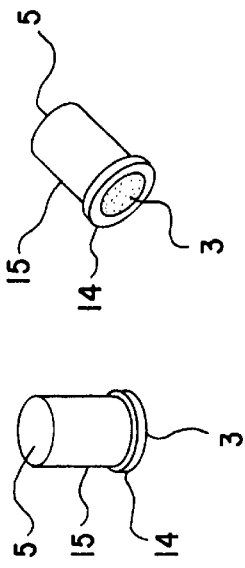

Fig.13
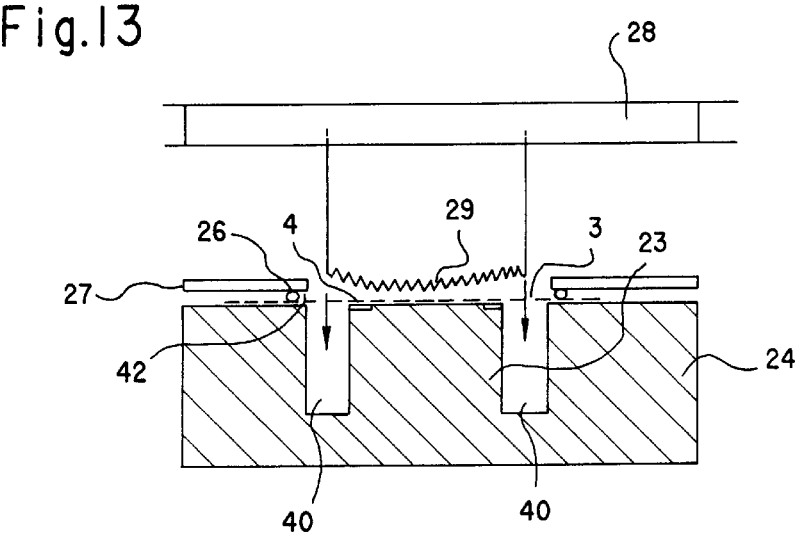
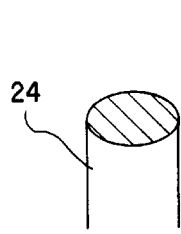
Fig.14(a)
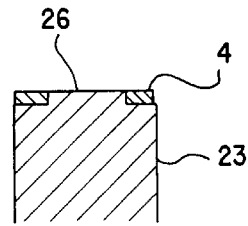
Fig.14(b)
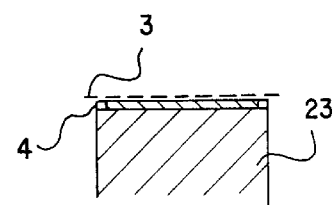
Fig.14(c)

METHOD AND A DEVICE FOR DIALYSIS OF LIQUID SAMPLES

CROSS REFERENCE TO RELATED APPLICATION

This application is continuation-in-part of application Ser. No. 08/840,221 filed on Apr. 11, 1997, abandoned. This application also claims priority from provisional patent application Ser. No. 60/070,119, filed on Dec. 31, 1997.

BRIEF HISTORY OF THE INVENTION

There are many devices currently available in the market for dialyzing small sample volumes. These devices require advanced preparation, including setting up before a sample can be dialyzed. A common feature of all such dialysis devices is that the sample must be transferred into the dialysis device and after dialysis the sample must be extracted from the dialysis device. Extraction, is accomplished using a pipetting device. U.S. Pat. No. 5,503,741 discloses one such dialysis device. Dialysis devices have also been fabricated by wrapping dialysis membranes on test tubes.

When dealing with small volume samples, one of the major problems is a loss of sample due to the transfer of samples to and from the dialysis equipment. When sample is present in such a small volume and not readily available the loss of sample becomes a critical consideration. Therefore, there is a need to develop a method and a device for dialysis that does not require the transfer of samples out of the dialyzer and which minimizes handling loss.

The present invention relates to a method and a device for the dialysis of sample in which the sample is dialyzed in a container device which can be centrifuged for collection of the dialyzed sample. The dialysis device or the part that collects the dialyzed sample can also be used to store the dialyzed sample which minimizes handling of the dialyzed sample. The present invention also relates to a method of fabricating a dialysis reservoir and a device for fabricating the dialysis reservoir.

SUMMARY OF THE INVENTION

This invention relates to a method and a device for dialysis of liquid samples. According to the present invention the liquid sample to be dialyzed is deposited into a dialysis reservoir, the dialysis reservoir has an open end, and the end opposite the open end is closed with a dialysis membrane, preferably a semipermeable dialysis membrane. The open end of the dialysis reservoir is adapted to receive a collection reservoir. The collection reservoir has an open end and the end opposite the open end is closed. The open end of the collection reservoir is adapted to receive the open end of the dialysis reservoir. Thus, the open ends of both the collection reservoir and the dialysis reservoir may be connected, engaged, mounted or brought together, either by free positioning or by screw mounting. The dialysis reservoir and the collection reservoir are adapted or designed to be subjected to centrifugal force by spinning in a centrifuge. Preferably, the collection reservoir is shaped like a centrifuge tube.

The dialysis reservoir is secured in a floatation device and floated in an appropriate dialysis buffer such that the dialysis membrane of the dialysis reservoir is in contact with the dialysis buffer. During dialysis, the collection reservoir may be either mounted, engaged or positioned on the open end of the dialysis reservoir or kept removed or separated from the open end of the dialysis reservoir.

After dialysis is complete, the dialysis reservoir is subjected to centrifugal force by positioning it in a centrifuge in the orientation which allows centrifugal migration of the dialyzed sample in the dialysis reservoir, through the open end of the dialysis reservoir, into the collection reservoir. If the collection reservoir was not positioned on the open end of the dialysis reservoir during the dialysis then the collection reservoir is positioned on the open end of dialysis reservoir prior to centrifugation of the dialysis reservoir for collection of dialyzed samples. The centrifugation allows the dialyzed sample in the dialysis reservoir to migrate into the collection reservoir for collection.

After collecting the dialyzed sample in the collection reservoir, the sample may be stored in the collection reservoir itself by placing a closure means on the open end of the collection reservoir.

In an embodiment of the present invention, the dialysis reservoir has outer and inner elements, wherein the outer element sleeves over the inner element, sandwiching or securing a dialysis membrane which forms the closed end opposite the open end of the dialysis reservoir.

The depositing of the dialyzable samples into the dialysis reservoir may be achieved either by directly depositing samples into the dialysis reservoir or depositing the sample first into the collection reservoir and then allowing the sample to migrate from the collection reservoir to the dialysis reservoir, either by inverting the open end of the collection reservoir into the open end of the dialysis reservoir in which case the sample will migrate under gravity into the dialysis reservoir or by centrifugation force, i.e. centrifuging the collection reservoir. For collecting the dialyzed sample after dialysis, the assembly of the dialysis reservoir and the collection reservoir is spun in a centrifuge which allows dialyzed sample to collect into the collection reservoir.

The present invention also relates to a method of fabricating a dialysis reservoir, a device for fabricating a dialysis reservoir, a device for fabricating the dialysis reservoir of the instant invention and a dialysis device of the instant invention. The method of fabricating a dialysis reservoir comprises: forming or providing a through-hole cap, having a depending skirt so that the through-hole is defined by a narrowing lip, the inside surface of the skirt being threaded; positioning a gasket through the skirt so that it contacts the inside surface of the lip; and fastening a dialysis membrane on the gasket.

A method of fabricating a dialysis reservoir comprises: forming or providing a through-hole cap having a depending skirt so that the through-hole is defined by a narrowing lip, the inside surface of said skirt, preferably, being threaded; and positioning a gasket having a dialysis membrane mounted within the gasket through the skirt so that it contacts the inside surface of the lip.

In an alternative embodiment, the method of fabricating a dialysis reservoir comprises: forming or providing a through-hole cap having a depending skirt so that the through-hole is defined by a narrowing lip, the inside surface of said skirt, preferably, being threaded; positioning a gasket through the skirt so that it contacts the inside surface of the lip: and fastening a dialysis membrane on the gasket. Preferably, the membrane is larger in diameter that the gasket.

A device for fabricating a dialysis reservoir comprises: one or more pillars, the pillar is provided to receive a gasket and a dialysis membrane; a means to hold the dialysis membrane securely in position on top of the pillar; and a means to engage a through-hole cap on top of the pillar wherein the open end of the through-hole cap sleeve over the pillar having the dialysis membrane and the gasket so that the dialysis membrane contacts the inside surface of the narrowing lip and closes the end opposite the open end of the dialysis reservoir.

A device for fabricating a dialysis reservoir, comprising: one or more pillars, the pillar is adapted to receive a gasket and a dialysis membrane;

a means to position a sheet of dialysis membrane on top of the pillar, the dialysis membrane is secured on the structure surrounding the pillar;

a membrane cutting means to cut the dialysis membrane to size and deposit on top of the pillar; and a pressure means to hold the dialysis membrane securely in position on top of the pillar and engage a through-hole cap defined by a skirt and a narrowing lip on top of the pillar so that the membrane contacts the inside surface of the narrowing lip.

The pillar has a diameter smaller than the open end of the through-hole cap, defined by a circumferential lip and a skirt, so that the cap sleeves freely over the pillar. The pillar may be provided with a geometrical structure to allow the gasket to be secured on top of the pillar. A sheet of dialysis membrane is positioned on top of the pillar, preferably, the sheet of dialysis membrane is held under tension on top of the pillar supported on the surrounding structure. A membrane cutting die is lowered on the membrane to cut the membrane to size and deposit the cut membrane on top of the pillar. Preferably, the diameter of the membrane cutting die is larger than the diameter of the gasket so that it cuts a piece of membrane larger in diameter than the diameter of the gasket.

Preferably, the means to hold the dialysis membrane securely in position on top of the pillar is a pressure means, preferably, a long pole like structure to put pressure on top of the membrane. The pressure means long pole is lowered on top of the pillar, sandwiching the membrane between the pole and the pillar.

After securing the dialysis membrane on top of the pillar, a through-hole cap is engaged on top of the pillar, depositing the assembly of the gasket and the membrane on the narrowing lip of the cap, closing the end opposite the open end with a dialysis membrane. The fabricated dialysis reservoir is removed from the top of the pillar.

The device of the present invention can also be used for assaying protein solutions containing agents that interfere with protein assays. According to the present method, the protein sample for assay will be deposited into the dialysis reservoir of the present invention and dialyzed to remove interfering agents from the protein solution. After dialysis, the device will be spun to collect the protein solution in the collection reservoir.

In some assays dialysis may lead to a small increase in the sample volume; the increase in the sample volume is determined by determining the difference in the weight of the dialyzer, containing sample, before and after dialysis. Reagents for protein assay are introduced into the collection reservoir for reaction with the protein solution collected in the collection reservoir. The reaction product of the protein solution is subjected to an optical density analyzer for the determination of protein concentration. The optical density of the reaction product is then compared with the optical density produced with a series of known concentrations of protein solutions.

The device of the present invention is a closed system and thus prevents loss of protein during dialysis and, subsequent to dialysis allows one-hundred percent recovery of the protein. Because there is no protein loss, the method can be used for protein assays where dialysis is required prior to protein assay.

The device of the present invention can also be used for isolation of genomic DNA. One of the major problems associated with isolation of high molecular weight genomic DNA is damage to DNA during isolation-manipulation steps. The device of the present invention can be used for isolating genomic DNA of high molecular weight. According to the method, cellular nuclei is isolated by grinding of cells and tissues using any popular method. The isolated nuclei, tissue sample, or cells is transferred into the dialysis reservoir of the present invention. The suspension of nuclei or sample is subjected to proteolytic digestion in the dialysis reservoir, preferably, using proteinase K, pepsin, trypsin, etc. After proteolytic digestion, the suspension is dialyzed in the dialysis reservoir. During dialysis small peptides and other impurities are dialyzed away, leaving behind, in the dialysis reservoir pure and high molecular weight genomic DNA. Since, digestion of nuclei and dialysis do not involve physical manipulation, the genomic DNA is protected from shear damage, resulting in high molecular weight DNA product.

BRIEF DESCRIPTION OF THE DRAWINGS

The invention is explained with the help of following drawings:

FIGS. 1(a)–1(b) show an embodiment of a dialysis reservoir, wherein (a) is a top view and (b) shows a cross sectional view.

FIG. 2 shows an embodiment of a collection reservoir.

FIGS. 3(a)–3(c) show various stages of assembly of the dialysis reservoir of FIG. 1 and the collection reservoir of FIG. 2; 3(a) shows a cross sectional view, 3(b) shows cross a sectional view after assembly and 3(c) shows the front view of the assembled dialysis reservoir and the collection reservoir.

FIG. 4 shows the assembled dialysis device of FIG. 3(c) floated in a dialysis tank for dialysis.

FIGS. 5(a)–5(b) show an alternative embodiment of the dialysis reservoir, 5(a) shows a top view and 5(b) shows a side view.

FIG. 6 shows an alternative embodiment of the collection reservoir.

FIG. 7 shows the assembly of the dialysis reservoir of FIG. 5 and the collection reservoir of FIG. 6.

FIG. 8. shows the dialysis reservoir of FIG. 5 floated in a dialysis tank for dialysis.

FIGS. 9(a)–9(c). show an alternative embodiment of the dialysis reservoir; 9(a) shows top view of the multifaceted dialysis reservoir, 9(b) shows a cross sectional view showing outer and inner elements of the dialysis reservoir and 9(c) shows the outer element sleeving over the inner element.

FIG. 10. Shows the dialysis reservoir of FIG. 9 assembled with the collection reservoir of FIG. 2.

FIG. 13 Shows elements of a device for fabricating a dialysis reservoir, having a pillar and a surrounding structure and a die for cutting a sheet of dialysis membrane to size and depositing the cut membrane on top of the pillar.

FIG. 14(a) shows a top view of the pillar having flat top surface, 14(b) shows a cross sectional view of an alternative embodiment of the pillar having a geometrical structure to secure a gasket on top of the pillar, and 14(c)a cross sectional view of a dialysis membrane and a gasket positioned on top of the pillar.

PREFERRED EMBODIMENT OF THE INVENTION

Figure 12A:
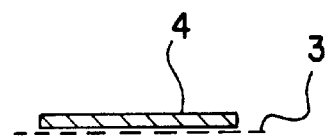
FIGS. 12(a)–12(b) show a cross sectional view of the relative size of a gasket and a dialysis membrane, wherein 12(a) shows that the dialysis membrane is larger in diameter than the gasket and 12(b) shows the edges of the dialysis membrane encircling the gasket.

In the embodiment of the invention shown in FIGS. 1–4, the dialysis device is made of a dialysis reservoir 2 (FIG. 1) and a collection reservoir 1 (FIG. 2). Preferably the dialysis reservoir 2 is a structure similar to a removable cap adapted with a dialysis membrane on the end opposite to the open end of the cap. The dialysis reservoir may be a cup shaped structure. The collection reservoir 1 is preferably shaped as a centrifuge tube. The open end of the dialysis reservoir 2 can be positioned on the open end of the collection reservoir 1.

The dialysis reservoir 2, as shown, has an open end 5 and an end opposite the open end. The end opposite the open end is closed with at least a dialysis membrane 3. The collection reservoir 1 has an open end 6 and an elongated body and an end 19 opposite the open end which is closed. The structure defines an elongated hollow area. Both the dialysis reservoir and the collection reservoir are provided with cooperating screw threads 7 so that, for instance, the open end of the dialysis reservoir 2 can be mounted or positioned on the open end of the collection reservoir 1, by screwing the two together.

In the dialysis reservoir 2, the end opposite the open end 5 has a circumferential lip 12 defining through bore 20. Connected to narrow lip 12 is a circumferential skirt member 14 creating joint 16, and positioned on the inside surfaces of the skirt are threads 7.

In fabrication, a dialysis membrane 3 is positioned through the open end 5 and positioned or centered to cover through-bore 20. In this manner the outer edge surfaces are defined by circumferential lip 12. Preferably positioned between a top surface of the dialysis membrane 3, and the inner surface of the narrowing lip 12 is a gasket 4. Thus, gasket 4 is placed near the surface of joint 16 and is simultaneously in contact with membrane 3. When the collection reservoir 1 is positioned on the open end of the dialysis reservoir 2, by screwing, as shown in FIG. 3(a) and in FIG. 3(b), the open end of the collection reservoir 1 presses against the gasket 4 and the membrane 3 making a leak proof seal between the membrane and the open end of the collection reservoir.

Figure 12B:
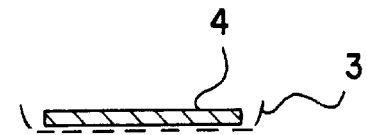

Preferably, the dialysis membrane 3 is larger in diameter than the gasket 4, as shown in FIG. 12(a). The dialysis membrane having a diameter larger than the diameter of the gasket allows the membrane to completely surround the gasket, consequently the gasket 4 resides within a nest created by the membrane 3, as shown in FIG. 12(b). Preferably, the dialysis membrane and the gasket may be fused or glued together so that they behave as a single integral item. In addition, the dialysis membrane forming the closed end opposite the open end of the dialysis reservoir may be fused into the body of the dialysis reservoir as an integral part. Alternatively, membrane and gasket may be manufacture by a process which allows creation of a gasket on the membrane itself.

In an alternative embodiment of the dialysis reservoir, as shown in cross section in FIG. 9, the dialysis reservoir 13 is made of an outer element 9 and an inner element 10. The outer element 9 is designed to sleeve over or telescopically receive the inner element 10 and the two pieces fit tightly or snugly together. Preferably, the outer 9 and the inner elements 10 are provided with a self locking structure to lock them relative to one another such as a bayonet mount (not shown in drawings). Alternatively, the outer element 9 and inner elements 10 are provided with a geometric structure to prevent the rotation of the outer element relative to the inner element or vice-versa. In a preferred embodiment, the outer and inner elements are multifaceted, as shown in FIG. 9, which shows the dialysis reservoir 13 with six sides. Other physical features such as uneven or gripping surface can also be provided on the outer and inner elements to prevent the rotation of the outer element relative to the inner element. In the outer element 9, the end opposite the open end 5 has a flange (circumferential lip) 12 which prevents the inner element 10 from passing through the outer element 9. The inner element 10 has a through bore which is aligned with through-bore 20 of the outer element and the inside face of element 10 is provided with screw threads 7 for mounting the dialysis reservoir 13 on the collection reservoir 1. For assembling the outer and inner elements into a dialysis reservoir 13, a dialysis membrane 3 is placed between the two elements, a gasket 4 may also be placed on the membrane 3 on the side nearer to the open end 5, the inner element 10 is pushed into the outer element 9 which sandwiches the dialysis membrane 3 and gasket 4 between the two elements, as shown in FIGS. 9(b) and 9(c). The circumferential lip 12 prevents the inner element 10 from passing through the outer element 9. The self locking structure as described above will lock the inner element in position and make a tight leak proof seal against the gasket and the membrane (not shown in FIGS.). Alternatively, when the open end of assembled dialysis reservoir 13 is positioned, by screwing, on the open end of the collection reservoir 1, the open end of the collection reservoir presses against the gasket 4 and the membrane 3 and makes a tight seal, as shown in FIG. 10.

Figure 11:
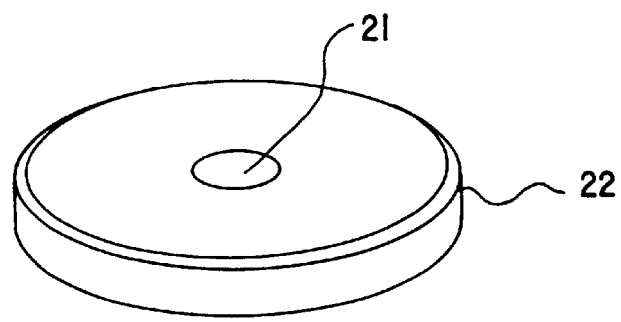
FIG. 11 Shows a flotation device for floating the dialysis reservoir.

In use for dialysis, a liquid sample is placed inside the hollow of the collection reservoir 1. The dialysis reservoir, defined by the circumferential lip and skirt (either reservoir 2 or 13) is secured onto collection reservoir 1, as shown in FIGS. 3 & FIG. 10. The dialysis device, the dialysis reservoir and collection reservoir assembly as shown in FIG. 3(c) and FIG. 10, is inverted and mounted on a doughnut-shaped floatation device 22 (see FIG. 11), as shown in FIG. 4, and placed in a dialysis tank 17 (FIG. 4 and FIG. 8) containing the appropriate dialysis buffer 18. The floatation device 22 receives the dialysis reservoir via hole 21. The dialysis membrane 3 in the dialysis reservoir contacts the dialysis buffer. When the collection reservoir is inverted, the liquid sample inside the collection reservoir migrates into the dialysis reservoir and rests on the dialysis membrane 3. The dialysis buffer is stirred during dialysis. Salts and other molecules within the dialysis reservoir migrate across the membrane 3 until an equilibrium is reached with the dialysis buffer in the dialysis tank. After the completion of dialysis process, the device assembly is removed from the floatation device 22. The collection reservoir is placed in a centrifuge and spun for a brief 5–10 seconds to collect the dialyzed sample in the bottom of the collection reservoir 1. Sample collection by centrifugation allows 100% recovery of the samples in the collection reservoir. After collecting the sample in the collection reservoir, the dialysis reservoir may be replaced with a closure means i.e., a cap for storage of the dialyzed sample in the collection reservoir for a later use.

In an alternative embodiment of the invention, the dialysis reservoir is made of a cup shaped structure 15 as shown in FIG. 5. The dialysis reservoir has an open end 5 and the end opposite the open end is closed with a dialysis membrane 3. The collection reservoir 8 (FIGS. 6 and 7) has an open end 6 and an end 19 opposite the open end is closed. Preferably, the collection reservoir 8 is a centrifuge tube, FIG. 6. The dialysis reservoir has a shoulder 14 which assists positioning of the open end of the dialysis reservoir 15 into the open end of the collection reservoir 8. The open end of the dialysis reservoir 15 is freely suspended into the open end of the collection reservoir 8, the dialysis reservoir rest on the shoulder 14 into the open end of the collection reservoir 8, as shown in FIG. 7. Shoulder 14 may also be provided to the open end of the collection reservoir to allow positioning of the open end of the dialysis reservoir.

For dialysis, a sample is placed into the dialysis reservoir 2 or 13 (FIG. 9c) and secured on the float 22 and floated in a dialysis tank 17 shown in FIG. 8, such that the membrane contacts the dialysis buffer. After dialysis is complete, the open end 5 of the dialysis reservoir 15 is assembled with the open end 6 of the collection reservoir 8, as shown in FIG. 7 and the whole assembly is spun for collection of the sample into the collection reservoir 8. After spinning, the dialysis reservoir 15 is disassembled from the collection reservoir 8 in order to reach the sample collected in the collection reservoir. The dialyzed sample may be stored in the collection reservoir by placing a closure means on the open end 6 of the collection reservoir 8. The dialysis device 13 of FIG. 9 could also be use as described in this paragraph.

FIG. 13 shows elements of the device for fabricating a dialysis reservoir. The device is provided with one or more pillar like structures 23 (FIG. 14a) and defined by a circumferential depending hollow 40 and a surrounding pillar support structure 24. The diameter of a pillar 23 is smaller than the open end of the dialysis reservoir, so that the pillar may freely pass through the end of the dialysis reservoir (a through-hole cap, defined by the circumferential lip and skirt). Preferably, the top of the pillar has a flat surface. The top of the pillar may be provided with a geometrical structure 25 to secure a gasket on top of the pillar, as shown in FIGS. 13 and 14(b). Structure 25 has a circular elevation having a diameter that allows the gasket 4 to seat on the elevation and is prevented from side-ways movement. See FIG. 14(b). The fabricating device preferably has an array of pillars to facilitate mass production.

In fabricating a dialysis reservoir a gasket 4 (FIG. 13) is positioned on top of the pillar and a sheet or a section of a dialysis membrane 3 is positioned on the pillar 23. The membrane 3 is secured to the top of the pillar 23 by applying a pressure devices on top of the membrane, which is supported on the surrounding structure 24. The pressure device is a plate 27 having a hollow middle section an having an 0-ring 26 fastened to the under-face of the plate near the inner circumferential surface 42 of the plate. When the plate is lowered on top of the membrane, the O-ring puts downward pressure on the membrane supported on the surrounding structure 24 as described above, and secures the membrane in place on top of the pillar 23. The membrane can be cut to size and deposited on top of the pillar by lowering a membrane cutting die, having cutting edges or teeth 29 as shown. As die 28 is lowered on top of the membrane 3 (as shown by the arrow), a circular piece of membrane is cut and deposited on top of pillar 23 (FIG. 14(c)).

Alternatively, the gasket 4 may be fabricated to possess a pre-mounted dialysis membrane 3 within the gasket. In such a case, it would not be necessary to place a sheet or section of membrane on top of the gasket and cut to size with die 28. Instead the gasket possessing such a membrane would be placed on top of the pillar.

Figure 15:
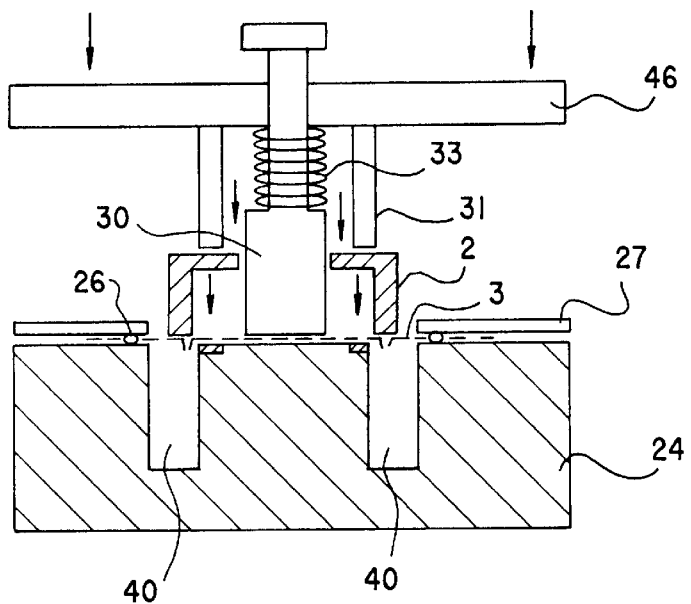
FIG. 15 shows further elements of the device for fabricating a dialysis reservoir, not shown in FIG. 13, having a means to hold a membrane on top of the pillar and concurrently engaging a through-hole cap on top of the pillar.
Figure 16A:
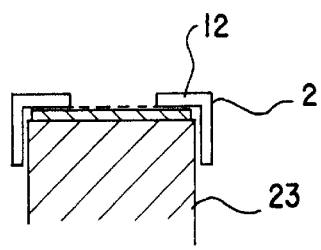
FIG. 16(a) shows a through-hole cap engaged on top of the pillar to receive the assembly of the gasket and the membrane and FIG. 16(b) shows a fabricated dialysis reservoir separated from the pillar shown in FIG. 16(a).
Figure 16B:
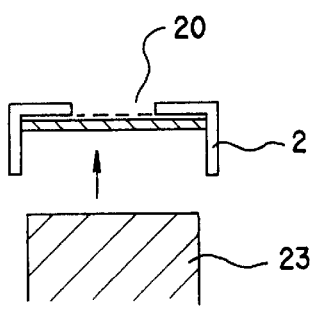

FIG. 15 shows further elements of the device for fabricating a dialysis reservoir. After a membrane and a gasket is deposited on top of pillar 23, a through-hole cap 2, defined by a circumferential lip and a skirt, is deposited on top of the membrane and the gasket. The open end 5 of the cap is near the top of the pillar. The cap 2 is engaged on top of the pillar by holding the membrane securely in position with a pushing element 46. Pushing element 46 is composed of spring piston 30 and push arms 31. The spring piston 30 and push arms 31 are connected to common pushing element 46 as shown. Spring 33 of spring piston 30 allows the spring piston 30 to exert a downward pressure on the membrane 3 (in the direction of the arrows) and concurrently allows the push-arm 31 to move downward (as the spring depresses) and push the cap so that is sleeves over the pillar, depositing the membrane and gasket on the circumferential lip 12 of the cap as shown in FIG. 16(a). The depending skirt of the reservoir is received within circumferential hollow 40. After assembly is completed the dialysis reservoir is separated from the pillar 23 as shown in FIG. 16(b).

For simplicity, the device of FIGS. 13 and FIG. 15 are shown separately, however, in fact the device can be and is constructed with elements to work cooperatively to facilitate the reservoir as above described.

What is claimed is:

1. A device for dialyzing liquid samples, comprising:
   a dialysis reservoir for receiving samples for dialysis, said reservoir having an open end and an end opposite the open end, the end opposite the open end closed with a member comprising a dialysis membrane, the dialysis reservoir is adapted for centrifugation;
   a collection reservoir having an open end and an end opposite the open end which is closed, the open end of the collection reservoir is fastened to the open end of the dialysis reservoir, and the collection reservoir is adapted for centrifugation;
   wherein the dialysis reservoir and the collection reservoir have means for securing the open end of the dialysis reservoir into the open end of the collection unit; and
   wherein the dialysis reservoir further comprises a gasket to contact the dialysis membrane, said gasket is positioned nearer to the open end of the dialysis reservoir and when the open end of the collection reservoir is engaged with the open end of the dialysis reservoir the open end of the collection reservoir presses against the gasket.

2. The device of claim 1 further comprising a floatation device for securing and floating the dialysis reservoir in a dialysis buffer in a manor that allows the dialysis membrane to contact the dialysis buffer.

3. The device according to claim 1 wherein the dialysis reservoir includes a shoulder for securely positioning the open end of the dialysis reservoir onto the open end of the collection reservoir.

4. The device according to claim 1 wherein the collection reservoir includes a shoulder for securely positioning the open ends of the dialysis reservoir onto the open end of the collection reservoir.

5. The device according to claim 1 wherein said collection reservoir is shaped as a centrifuge tube.

6. The device according to claim 1 wherein the dialysis reservoir is mounted on the collection reservoir during dialysis.

7. The device according to claim 6 wherein the collection reservoir is a centrifuge tube.

8. A method for dialyzing a liquid sample with the claim 1 device, comprising:

depositing a sample for dialysis into a dialysis reservoir, the dialysis reservoir having an open end and the end opposite the open end is sealed with a dialysis membrane, the dialysis reservoir is designed to be subjected to centrifugal force in a centrifuge;

positioning the dialysis reservoir in a dialysis buffer such that the dialysis membrane of the dialysis reservoir makes contact with the dialysis buffer; and after dialysis is complete, centrifuging the dialysis reservoir to allow migration of the dialyzed sample through the open end of the dialysis reservoir into a collection reservoir positioned on the open end of the dialysis reservoir.

9. A method according to claim 8 wherein the dialysis sample is deposited directly into the dialysis reservoir and after dialysis the sample is collected into the collection reservoir by positioning the open ends of the collection reservoir on the open end of the dialysis reservoir and subjecting the assembly to centrifugation in the orientation which allows centrifugal migration of the dialyzed sample through the open end of the dialysis reservoir into the collection reservoir.

10. The device of claim 1, wherein the means for securing the open end of the dialysis reservoir into the open end of the collection unit is a screw thread means.

11. The device of claim 1, wherein the dialysis membrane and the gasket are fused and/or glued together so that they are single integral item.

12. The device of claim 1, wherein the dialysis membrane is fused into the body of the dialysis reservoir.

13. The device of claim 1, wherein the gasket is adjacent to the membrane.

14. A device for dialyzing liquid samples, comprising:

a dialysis reservoir for receiving samples for dialysis, said reservoir having an open end and an end opposite the open end, the end opposite the open end closed with a member comprising a dialysis membrane, the dialysis reservoir is adapted for centrifugation;

a collection reservoir having an open end and an end opposite the open end which is closed, the open end of the collection reservoir is fastened to the open end of the dialysis reservoir, and the collection reservoir is adapted for centrifugation wherein the dialysis reservoir further comprises an outer element sleeving over an inner element such that the outer element and inner element fit tightly or snugly together to form the dialysis reservoir;

wherein the dialysis membrane is secured between the outer element and the inner element to seal the end opposite the open end of the dialysis reservoir.

15. The device according to claim 14 wherein the dialysis reservoir and the collection reservoir have screw thread means for securing the open end of the dialysis reservoir into the open end of the collection reservoir.

16. The device according to claim 14 wherein said outer element and said inner element have structure elements to restrict the rotation of the outer element sleeving over the inner element.

17. The device according to claim 6 wherein said inner element has screw threads for engaging the open end of the collection reservoir.

18. The device according to claim 14 wherein a gasket contacts the dialysis membrane and the collection reservoir.

19. The device according to claim 14 wherein a gasket means is secured between the outer and the inner elements such that said gasket means is nearer to the open end of the dialysis reservoir and presses against the dialysis membrane and the collection reservoir.

20. The device according to claim 7 wherein the dialysis membrane is fused into the body of the dialysis reservoir as an integral part.

* * * * *